US00PP18926P2

(12) United States Plant Patent
Smith

(10) Patent No.: US PP18,926 P2
(45) Date of Patent: Jun. 10, 2008

(54) ***CHRYSANTHEMUM* PLANT NAMED 'YOJILLIAN'**

(50) Latin Name: *Chrysanthemum×morifolium*
Varietal Denomination: Yojillian

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/641,400

(22) Filed: Dec. 18, 2006

(51) Int. Cl.
*A01H 5/00* (2006.01)

(52) U.S. Cl. ..... Plt./287

(58) Field of Classification Search ..... Plt./287
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Chrysanthemum* plant named 'Yojillian', characterized by its compact, upright and outwardly spreading plant habit; freely branching habit; dense and full plant habit; uniform and freely flowering habit; decorative-type inflorescences with elongated oblong to ligulate-shaped ray florets; lavender-colored ray florets; and natural season flowering about September 12$^{th}$ in the Northern Hemisphere.

1 Drawing Sheet

Botanical designation: *Chrysanthemum×morifolium.*
Cultivar denomination: 'Yojillian'.

CROSS-REFERENCED TO CO-PENDING APPLICATIONS

Title: Chrysanthemum Plant Named 'Yodarlene'. Applicant: Mark A. Smith Filed concurrently.

BACKGROUND OF THE INVENTION

The present invention relates to a new and distinct cultivar of *Chrysanthemum* plant, botanically known as *Chrysanthemum×morifolium,* commercially grown as a garden *Chrysanthemum* and hereinafter referred to by the name 'Yojillian'.

The objective of the breeding program is to create new garden-type *Chrysanthemum* cultivars having inflorescences with desirable inflorescence forms, attractive floret colors and good garden performance.

The new *Chrysanthemum* originated from a cross-pollination made by the Inventor in January, 2001, in Salinas, Calif. of a proprietary selection of *Chrysanthemum×morifolium* identified as code number 98-M307, not patented, as the female, or seed, parent with a proprietary selection of *Chrysanthemum×morifolium* identified as code number 98-M394, not patented, as the male, or pollen, parent. The new *Chrysanthemum* was discovered and selected by the Inventor as a single flowering plant within the progeny of the stated cross-pollination in a controlled environment in Alva, Fla. in September, 2003.

Asexual reproduction of the new *Chrysanthemum* by vegetative cuttings was first conducted in Alva, Fla. in December, 2003. Asexual reproduction by cuttings has shown that the unique features of this new *Chrysanthemum* are stable and reproduced true to type in successive generations.

SUMMARY OF THE INVENTION

Plants of the cultivar Yojillian have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yojillian'. These characteristics in combination distinguish 'Yojillian' as a new and distinct garden *Chrysanthemum* cultivar:

1. Compact, upright and outwardly spreading plant habit.
2. Freely branching habit; dense and full plant habit.
3. Uniform and freely flowering habit.
4. Decorative-type inflorescences with elongated oblong to ligulate-shaped ray florets.
5. Lavender-colored ray florets.
6. Natural season flowering about September 12$^{th}$ in the Northern Hemisphere.

In side-by-side comparisons conducted in Alva, Fla., plants of the new *Chrysanthemum* differed from plants of the female parent selection in the following characteristics:

1. Plants of the new *Chrysanthemum* flowered earlier than plants of the female parent selection when grown under natural season conditions.
2. Plants of the new *Chrysanthemum* flowered more uniformly than plants of the female parent selection.
3. Ray florets of plants of the new *Chrysanthemum* were lavender in color whereas ray florets of plants of the female parent selection were yellow in color.

In side-by-side comparisons conducted in Alva, Fla., plants of the new *Chrysanthemum* differed from plants of the male parent selection in the following characteristics:

1. Plants of the new *Chrysanthemum* were more mounded than plants of the male parent selection.

2. Plants of the new *Chrysanthemum* flowered earlier than plants of the male parent selection when grown under natural season conditions.
3. Plants of the new *Chrysanthemum* and the male parent selection differed in inflorescence form.
4. Plants of the new *Chrysanthemum* and the male parent selection differed in ray floret coloration as plants of the male parent selection had purple-colored ray florets.

Plants of the new *Chrysanthemum* differ from plants of the cultivar Yodarlene, disclosed in a U.S. Plant patent application Ser. No. 11/641,397 filed concurrently, primarily in time to flower and ray floret coloration.

Plants of the new *Chrysanthemum* can be compared to plants of the *Chrysanthemum* cultivar Debonair, disclosed in U.S. Plant Pat. No. 5,324. In side-by-side comparisons conducted in Alva, Fla., plants of the new *Chrysanthemum* differed from plants of the cultivar Debonair in the following characteristics:

1. Plants of the new *Chrysanthemum* were more mounded than plants of the cultivar Debonair.
2. Plants of the new *Chrysanthemum* flowered more uniformly than plants of the cultivar Debonair.
3. Plants of the new *Chrysanthemum* had smaller inflorescences than plants of the cultivar Debonair.
4. Plants of the new *Chrysanthemum* and the cultivar Debonair differed slightly in ray floret coloration.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Yojillian.'.

The photograph at the top of the sheet is a close-up view of typical inflorescences of 'Yojillian'.

DETAILED BOTANICAL DESCRIPTION

The aforementioned photographs and following observations and measurements describe plants grown in Pendleton, S.C. during the summer in an outdoor nursery and under conditions and practices which approximate those generally used in commercial garden *Chrysanthemum* production. During the production of the plants, day temperatures averaged 32° C. and night temperatures averaged 21° C. Plants were grown in 15-containers and exposed to long day/short night conditions for about three weeks, then exposed to natural season photoinductive conditions. Plants used in the photographs and for the description were about three months old. In the following description, color references are made to The Royal Horticultural Society Colour Chart, 1995 Edition, except where general terms of ordinary dictionary significance are used.

Botanical classification: *Chrysanthemum×morifolium* cultivar Yojillian.

Parentage:

*Female, or seed, parent.*—Proprietary selection of *Chrysanthemum×morifolium* identified as code number 98-M307, not patented.

*Male, or pollen, parent.*—Proprietary selection of *Chrysanthemum×morifolium* identified as code number 98-M394, not patented.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Herbaceous decorative-type garden *Chrysanthemum*. Stems upright and outwardly spreading giving a uniformly mounded appearance to the plant. Freely branching habit, about seven to eight lateral branches develop after removal of terminal apex (pinching) each with numerous secondary laterals; dense and full plant habit. Strong and vigorous growth habit.

*Plant height.*—About 21 cm.

*Plant width.*—About 37 cm.

*Lateral branches.*—Length: About 18 cm. Diameter: About 7 mm. Internode length: About 1.8 cm. Strength: Strong. Texture: Pubescent. Color: 148A.

*Leaves.*—Arrangement: Alternate, simple. Length: About 3.8 cm. Width: About 2.8 cm. Apex: Acute to cuspidate. Base: Attenuate. Margin: Palmately lobed, sinuses between lateral lobes mostly divergent. Texture, upper and lower surfaces: Fine pubescence; veins prominent on lower surface. Color: Developing and fully expanded foliage, upper surface: 147A; venation, 147B. Developing and fully expanded foliage, lower surface: Darker than 147B; venation, 147B. Petiole: Length: About 5 mm. Diameter: About 3 mm. Texture, upper and lower surfaces: Pubescent. Color, upper surface: 147A to 147B. Color, lower surface: 147B.

Inflorescence description:

*Appearance.*—Decorative-type inflorescence form with elongated oblong to ligulate-shaped ray florets. Inflorescences borne on terminals above foliage. Disk and ray florets arranged acropetally on a capitulum. Inflorescences not fragrant.

*Flowering response.*—Early flowering habit; under natural season conditions, plants flower about September 12$^{th}$ in the Northern Hemisphere. At other times of the year, inflorescence initiation and development can be induced under short day/long night conditions (at least 13.5 hours of darkness).

*Postproduction longevity.*—Inflorescences maintain good color and substance for about 3.5 weeks in an outdoor nursery.

*Quantity of inflorescences.*—About 13 to 14 inflorescences develop per lateral branch.

*Inflorescence bud.*—Height: About 1.1 cm. Diameter: About 9 mm. Shape: Oblate. Color: 75C.

*Inflorescence size.*—Diameter: About 4 cm. Depth (height): About 1.7 cm. Receptacle diameter: About 1.6 cm. Receptacle height: About 4 mm.

*Ray florets.*—Shape: Elongated-oblong to ligulate. Orientation: Initially upright, then about 90° from vertical or perpendicular to peduncle. Aspect: Initially incurved, then mostly concave. Length: About 2 cm. Width: About 5 mm. Apex: Broadly acute. Base: Acute. Margin: Entire. Texture, upper and lower surfaces: Smooth, glabrous, satiny. Number of ray florets per inflorescence: About 180 arranged in about 16 whorls. Color: When opening, upper surface: 77B. When opening, lower surface: 75C. Fully opened, upper surface: 78C. Fully opened, lower surface: 75D.

*Disc florets.*—None observed.

*Phyllaries.*—Number of phyllaries per inflorescence: About 26 arranged in about three whorls. Length: About 6 mm. Width: About 3 mm. Shape: Elliptic. Apex: Acute. Base: Truncate. Texture, upper surface: Smooth, waxy. Texture, lower surface: Pubescent. Color, upper surface: Close to 143B. Color, lower surface: Close to 144A.

*Peduncles.*—Length: About 5.3 cm. Diameter: About 2.5 mm. Angle: About 50° to 70° from vertical. Strength: Strong. Texture: Pubescent; longitudinally ridged. Color: Close to 148A.

*Reproductive organs.*—Androecium: None observed. Gynoecium: Pistil length: About 4 mm. Stigma shape: Bi-parted. Stigma color: Close to 7A. Style length: About 2 mm. Style color: Close to 145C. Ovary color: Close to 145D.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and to tolerate temperatures from about 0° C. to about 38° C.

It is claimed:

1. A new and distinct *Chrysanthemum* plant named 'Yojillian' as illustrated and described.

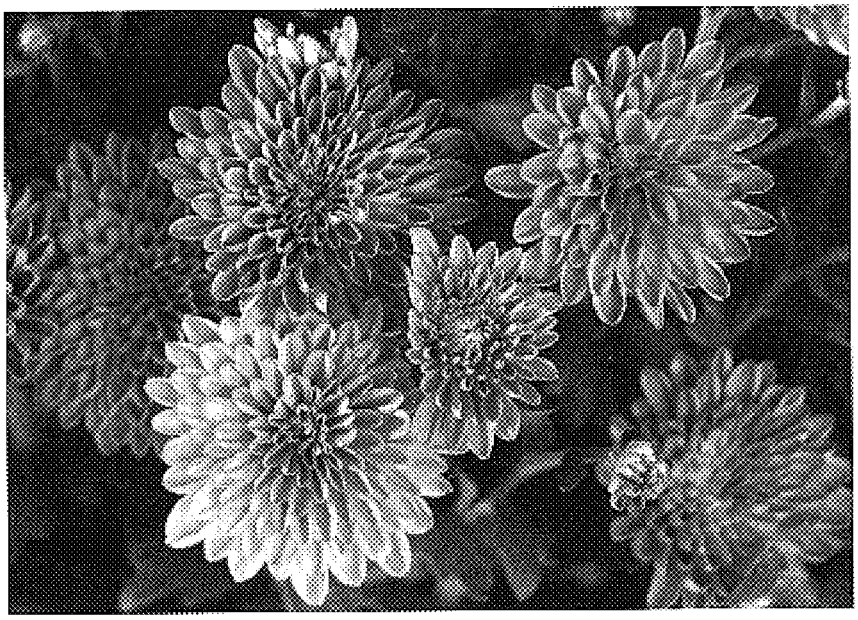
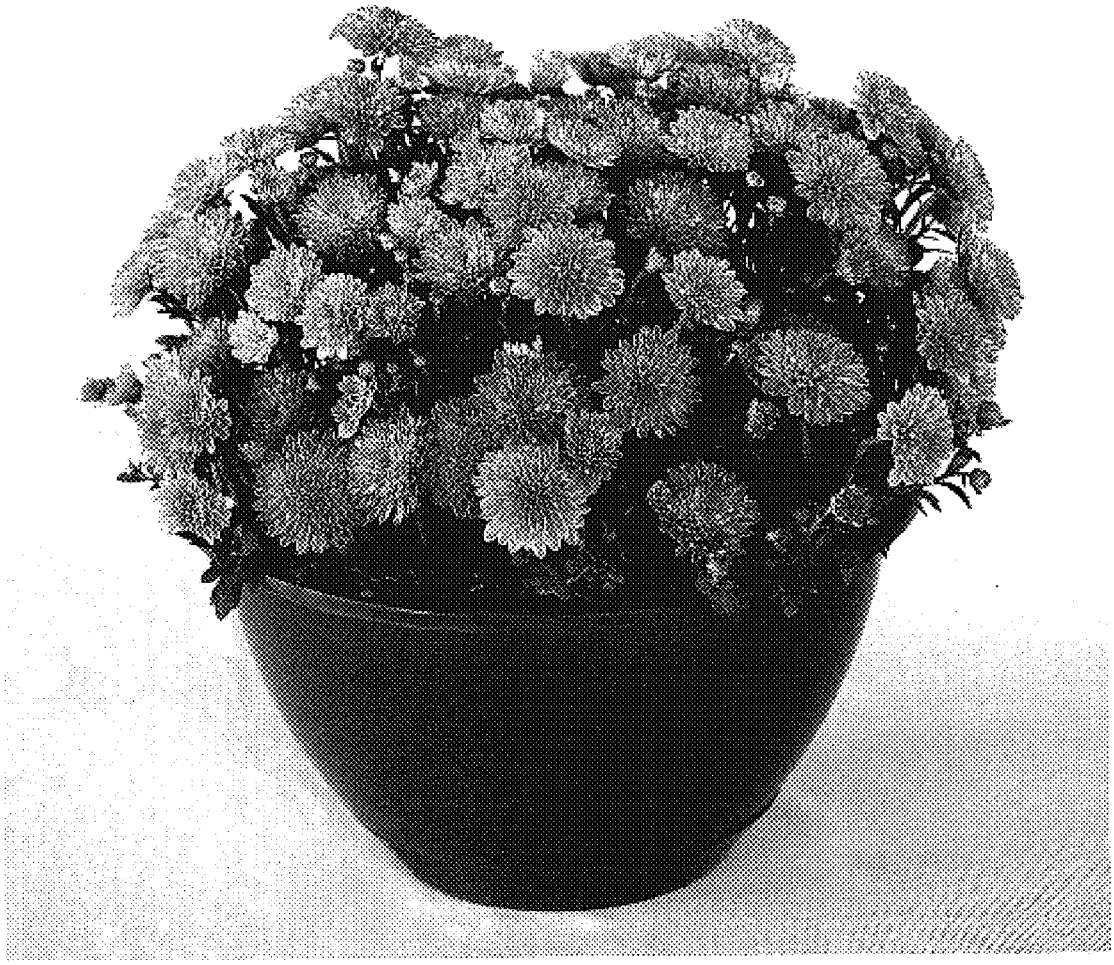

* * * * *